United States Patent [19]
Zaki

[11] Patent Number: 5,098,300
[45] Date of Patent: Mar. 24, 1992

[54] SURE CONTACT APPLIANCE AND PRECISION INSERTS

[76] Inventor: Tarek O. Zaki, 1248 Gunn Hall Dr., Ste. 102, Virginia Beach, Va. 23454

[21] Appl. No.: 718,756

[22] Filed: Jun. 21, 1991

[51] Int. Cl.[5] .................................................. A61C 5/04
[52] U.S. Cl. ...................................... 433/229; 433/39; 433/226
[58] Field of Search ................. 433/215, 226, 229, 39, 433/149

[56] References Cited

U.S. PATENT DOCUMENTS

| | | | |
|---|---|---|---|
| 2,035,347 | 3/1936 | Shotton | 433/226 |
| 2,538,486 | 1/1951 | Tofflemire | 433/226 |
| 2,611,182 | 9/1952 | Tofflemire | 433/39 |
| 3,423,835 | 10/1966 | Mattern | 433/39 |
| 3,896,553 | 7/1975 | Fagelmann . | |
| 4,449,928 | 5/1984 | von Weissenfluh | 433/40 |
| 4,514,174 | 4/1985 | Dougherty | 433/220 |
| 4,600,389 | 7/1986 | Schwartz | 433/217.1 |
| 4,696,646 | 9/1987 | Maitland | 433/229 |
| 4,726,770 | 2/1988 | Kurer | 433/39 |
| 4,744,759 | 5/1988 | Bowen | 433/218.1 |
| 4,747,777 | 5/1988 | Ward | 433/39 |
| 4,971,558 | 11/1990 | Jacobi | 433/226 |

OTHER PUBLICATIONS

Improving Composites (A Look at Glass-Ceramic Inserts)-The Journal of the American Dental Association-Mar. 1991.

Primary Examiner—Cary E. O'Connor
Attorney, Agent, or Firm—Cushman, Darby & Cushman

[57] ABSTRACT

An appliance is provided which can safely and securely carry one or more inserts into the cavity to be filled, apply a constant positive pressure against an adjacent tooth, and allow the dentist to adjust the location and spacing of the insert(s) and the amount of pressure exerted by the proximal insert against the adjacent tooth, as desired. Following initial placement of the insert, the insert is secured in a desired position and maintained in that position during the entire filling process so that both of the practitioner's hands are free to carry out the polymer delivery and polymerization process.

17 Claims, 5 Drawing Sheets

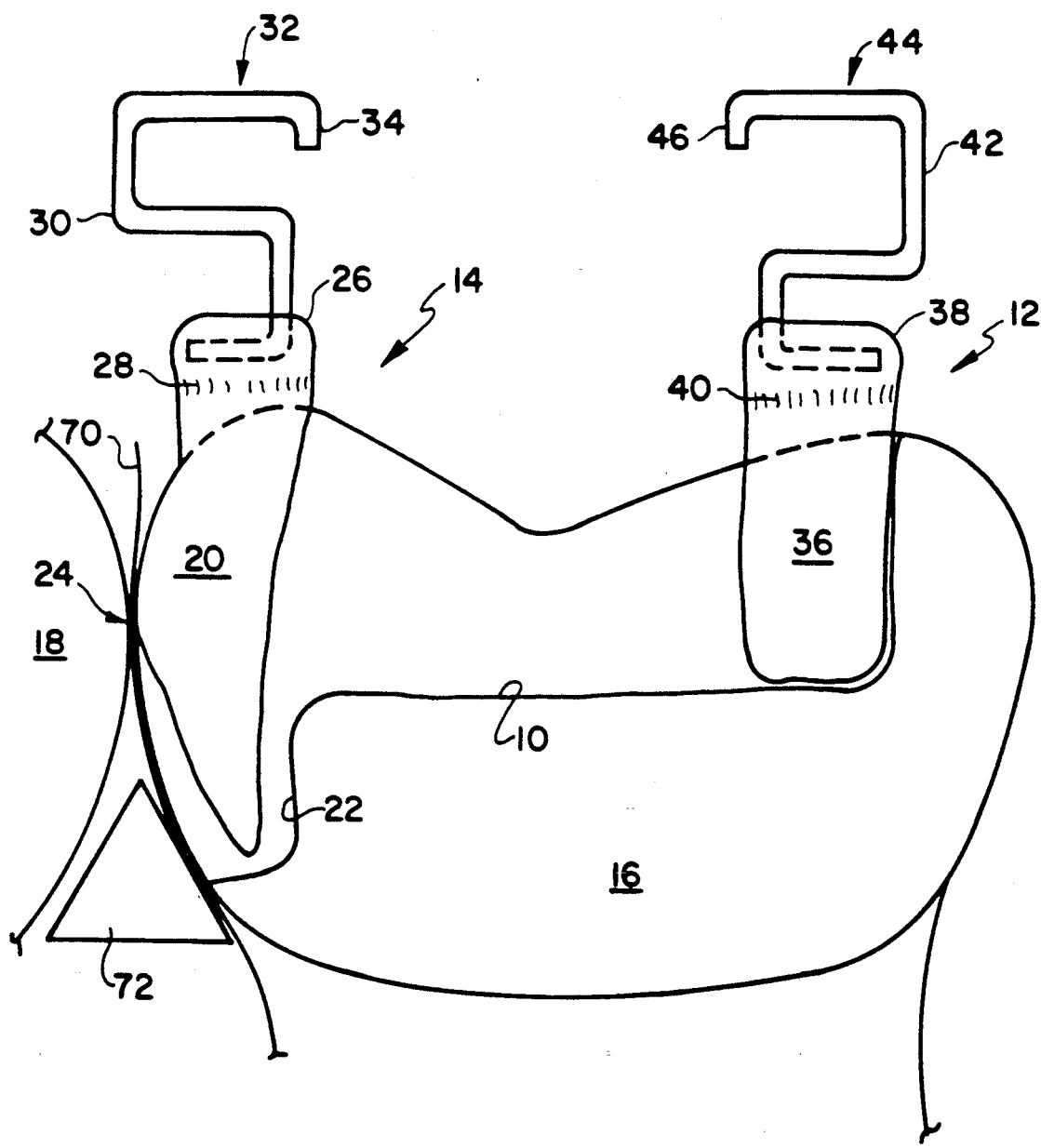

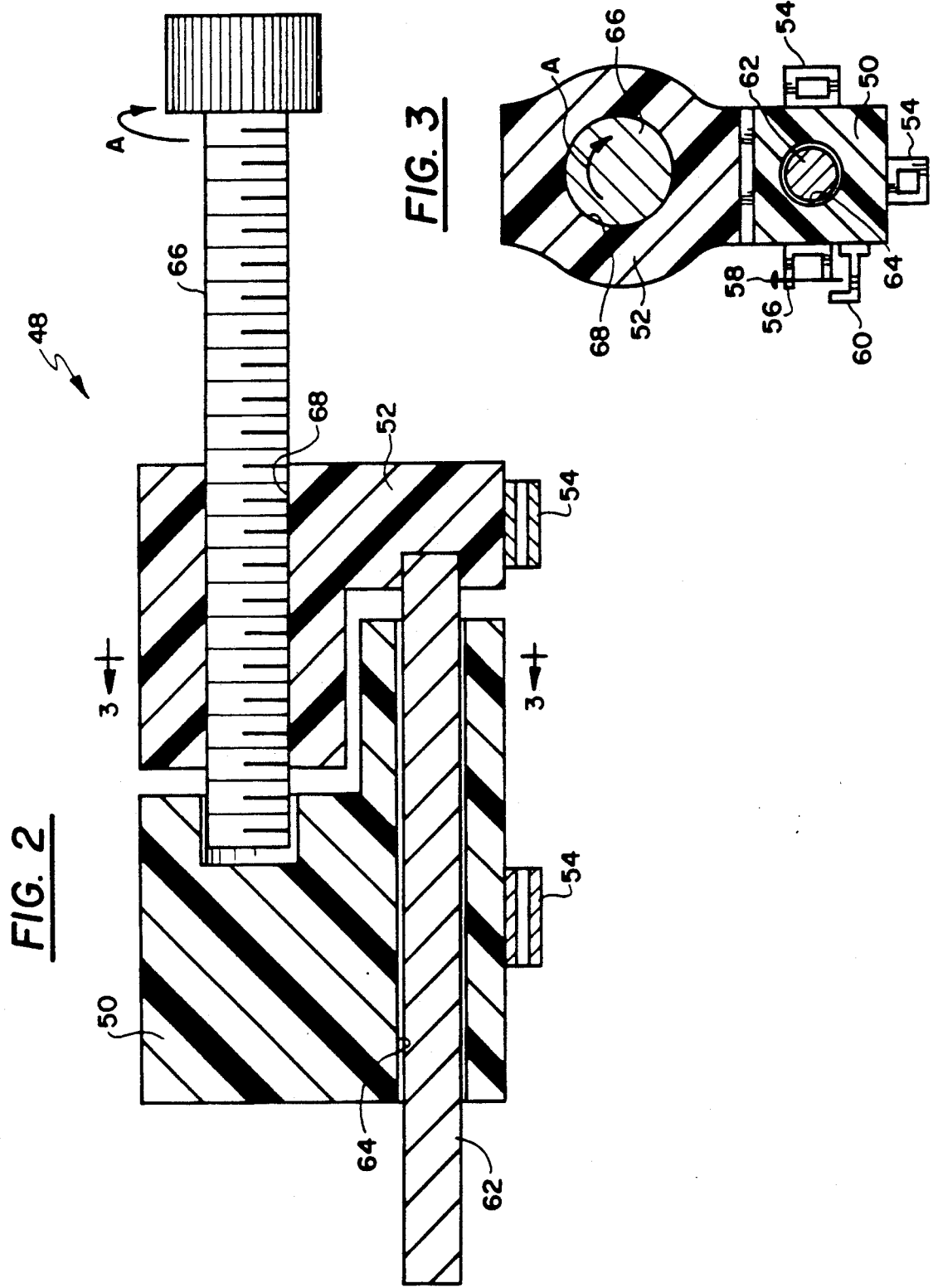

SURE CONTACT APPLIANCE AND PRECISION INSERTS

BACKGROUND OF THE INVENTION

1. Field of the Invention

The present invention relates to an appliance and method for filling and restoring teeth.

2. Description of the Related Art

A century ago people died from dental abscesses. Advancements in all branches of dentistry have made it possible to avoid the breakdown of both the dental and periodontal structures. The focus now is shifting towards cosmetics, producing filling materials which duplicate the appearance of natural teeth so that teeth appear straight, white and healthy. Indeed, the demand for natural tooth-colored or esthetic restorations in lieu of tooth-colored or esthetic restorations in lieu of silver an gold colored fillings is on the rise. Some patients demand such esthetic restorations because the natural color makes them virtually undetectable. Other patients have become concerned by the recent reports of potential hazards of silver amalgam fillings and, therefore, are interested in viable alternatives thereto. To date, however, such intra-orally cured composites however are yet to be the ideal filling material. Polymerization shrinkage and difficulty in obtaining proximal contact and finishing the proximal areas are but a few of the difficulties reported with techniques for composites. Indeed, such restorations also exhibit inferior wear resistance and marginal strength.

Some researchers have addressed the drawbacks of direct esthetic fillings (intra-orally polymerized) by resorting to either an indirect or an indirect-direct technique to allow for optimal polymerization conditions, be they heat, pressure or both.

Among the advantages of direct, esthetic restorations are the possibility for a conservative cavity outline. Indeed there is no need for removal of sound tooth structure in order to allow for a path of insertion and removal of a restoration. No luting agent is needed so there is one less variable with which the dentist must deal. No impressions and lab work are required and therefore it is less expensive and there are less variables. Finally, there is no requirement for temporization and one visit is sufficient for the filling procedure.

Of the disadvantages of direct esthetic Cl II and Cl IV restorations are greater difficulty in achieving good interproximal contact due to inability to condense the restorative material against the matrix band (as in the case of amalgam and gold foil restorations), weaker restorative material which will wear faster resulting in plunger cusps and progressively loosening interproximal contact, and greater technique sensitivity especially to moisture contamination.

The indirect technique's advantages lie in its ability to minimize the disadvantage of the direct technique. The filling can be fabricated of composites that are cured under heat and/or pressure, and are therefore superior in strength, durability and friction resistance. On the other hand, the disadvantages lie in the need to have divergent walls which may dental the unnecessary removal of sound tooth structure, the necessity of lab work and cementation of the final restoration and sometimes the necessity of temporization.

Other researchers have sought to employ glass ceramic inserts to provide a scaffold against which the polymerizable material is built up. It is anticipated that ceramic inserts will decrease micro leakage, increase stiffness an durability of the composite and add dimensional stability to the remaining tooth crown during hardening and function. One known system provides components for toothy restoration in the form of a preformed body which is used to create a contact with an adjacent tooth. The preformed body or insert is engaged with a handheld tool and is manually held in position during the filling/polymerization process. That technique disadvantageously occupies one of the dental practitioner's hands and thus can be difficult to quickly and effectively accomplish. In addition, such a manually held insert will not reliably provide a constant positive pressure against the next adjacent tooth while polymerization of the composite around the insert occurs. Fluctuation of contact pressure during that critical stage may be detrimental to the strength of the union between the composite and the insert on the one hand and the composite/insert complex and surrounding tooth structure on the other.

SUMMARY OF THE INVENTION

It is an object of the present invention to provide a prefabricated contact area in conjunction with light cured composite to overcome the above-noted problems of silver fillings and currently used composite fillings. The prefabricated contact area provides a positive contact against an adjacent tooth when positively urged against that tooth using a device anchored to the cavity of the tooth. The prefabricated insert also acts as a guide and scaffolding that will facilitate the proper molding of the proximal surface by the dental matrix. The overall shrinkage in the proximal box will be much less because he area occupied by the prefabricated insert will not shrink. It also acts as a condenser (for the unpolymerizd filling) that will not be retracted occlusally once it is integrated into the filling. This reduces the porosity of the non-insert component of the filling and enhances the marginal adaptability.

Thus, the present invention provides a direct technique for a better, more durable composite restoration which will maximize benefits for both dentists and patients.

The present invention provides an appliance which can safely and securely carry one or more inserts into the cavity to be filled, apply a constant positive pressure against an adjacent tooth (teeth), and allow the dentist to adjust the location an spacing of the insert(s) and the amount of pressure exerted by the proximal inset against the adjacent tooth, as desired. Following initial placement of the insert(s), both of the practitioner's hands are free to carry out the rest of the polymer delivery, the initial carving and polymerization process. Stability of the insert during polymerization of the composite is no longer a concern because the insert will be secured in a desired disposition and maintained in that position during the entire filling process.

In the case of MOD cavities, mesial and distal inserts can be placed with the same ease and predictable result simultaneously. The additional time if any is minimal as compared to that for a single proximo-occlusal filling. An occlusal insert, of course, can be provided as well.

The appliance therefore allows the operator to manipulate the insert(s) of the invention into the desired position(s) with ease and precision. The filling process can be conducted with minimal risk of the insert falling into the mouth and being contaminated, swallowed or inhaled by the patient. Moreover, following completion of the filling process or immediately prior thereto, the insert can be severed from the mounting and pressure applying system so that no extrinsic material remains in the final composite/insert complex.

Other objects, features and characteristics of the present invention, as well as the methods of operation and functions of the related elements of the structure and the combination of parts and economies of manufacture, will become more apparent upon consideration of the following detailed description and the appended claims with reference to the accompanying drawings, all of which form a part of this specification, wherein like reference numerals designate corresponding parts in the various figures.

BRIEF DESCRIPTION OF THE DRAWINGS

FIG. 1 is a schematic elevational view of a pair of inserts provided in accordance with the present invention disposed within a tooth, with the mounting appliance omitted for clarity;

FIG. 2 is a schematic cross-sectional view of a mounting appliance provided in accordance with one embodiment of the invention;

FIG. 3 is a schematic cross-sectional view of a mounting appliance of the type shown in FIG. 2 taken in the direction of the line 3—3 in FIG. 2;

DETAILED DESCRIPTION OF THE PRESENTLY PREFERRED EXEMPLARY EMBODIMENTS

Figure 4:
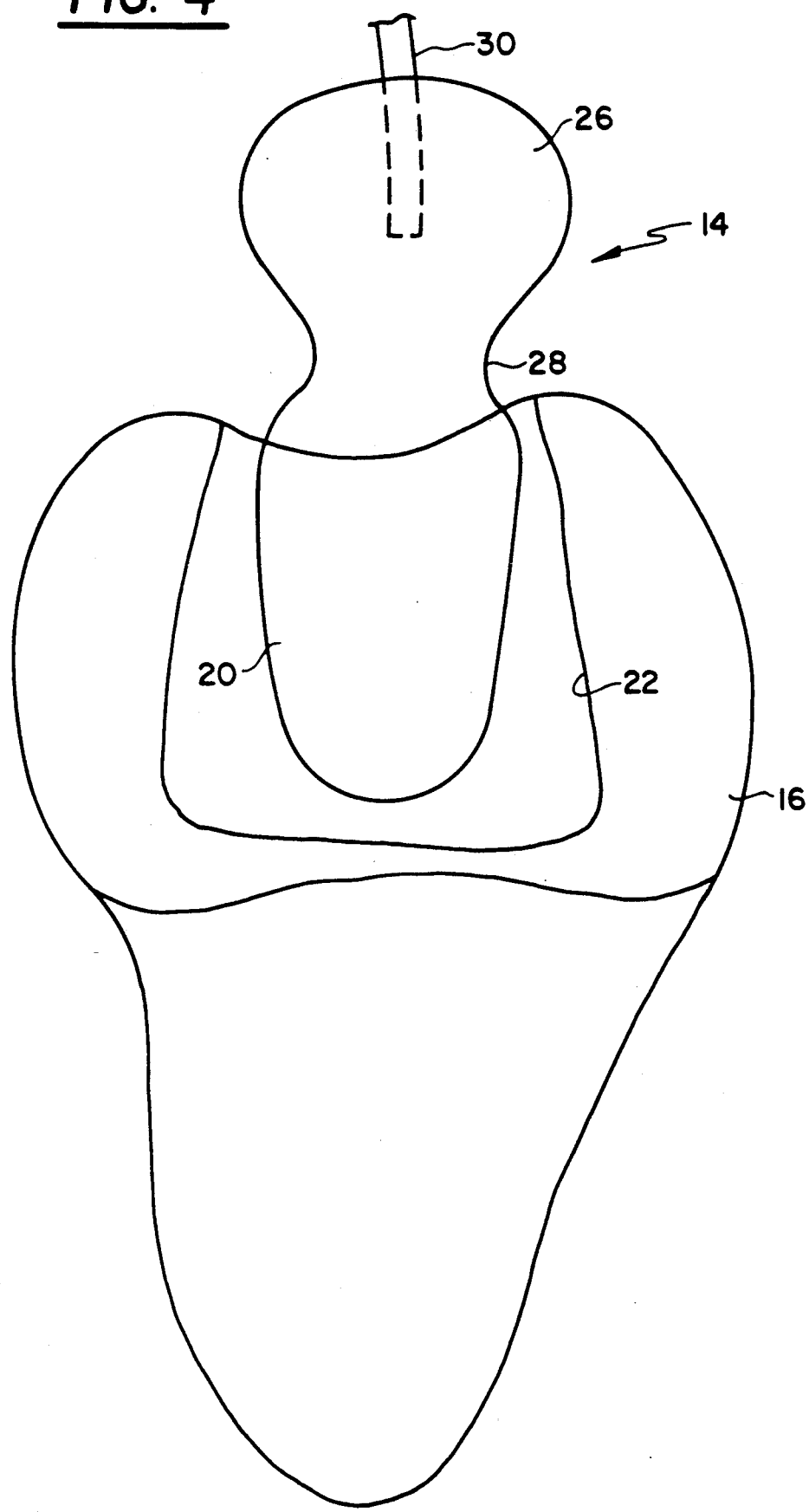
FIG. 4 is a schematic end elevational view of a proximal insert disposed in the proximal box of a tooth to be restored.

In accordance with a first, currently preferred embodiment of the present invention, a pair of insert are provided for placement within a prepared cavity 10 to be filled. One of the inserts, the occlusal insert 12, is adapted to be disposed at one peripheral edge of the filling and the proximal insert 14 is configured for and disposed at the opposite end of the tooth 16 in facing relation to the next adjacent tooth 18 (FIG. 1). The inserts are respectively coupled to a sure contact appliance (not shown in FIG. 1) provided in accordance with the invention which properly positions the insert(s) 12, 14 in the cavity 10 to be filled, urges the proximal insert 14 against the next adjacent tooth 18 with a desired, constant force, and holds the insert(s) 12,14 in that position and with that force during the filling/polymerizing process, as detailed herein below.

Figure 5:
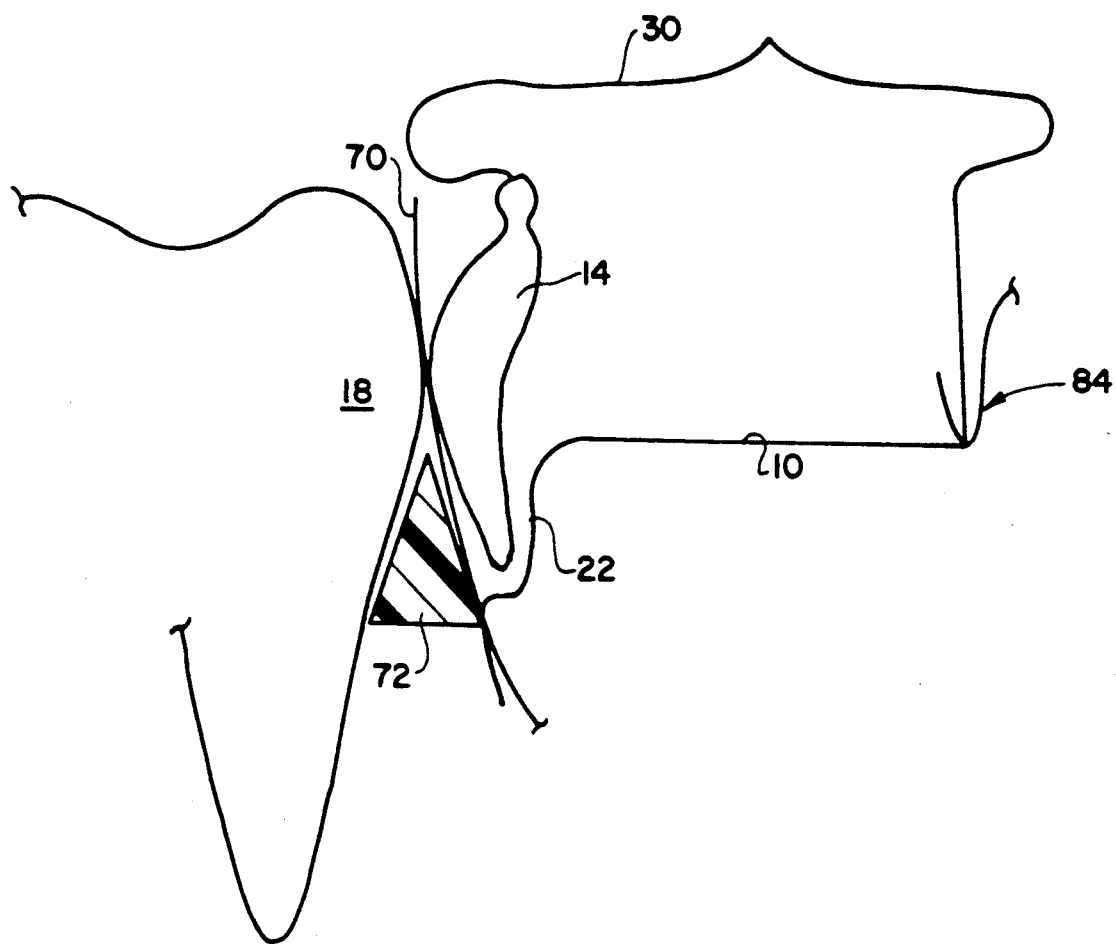
FIG. 5 is a schematic elevational view of an alternate embodiment of the present invention.
Figure 6:
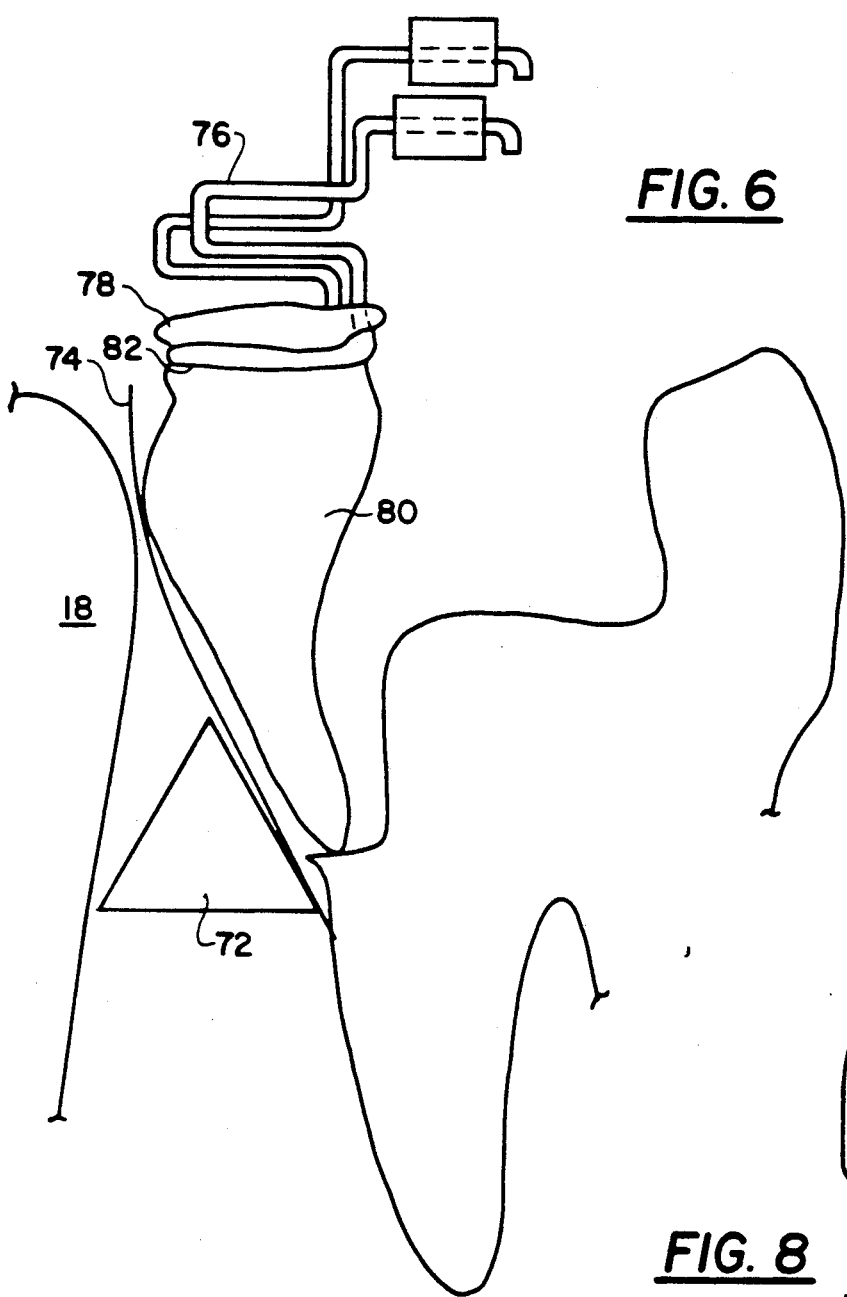
FIG. 6 is a schematical elevational view of a further alternate embodiment of the invention.
Figure 7:
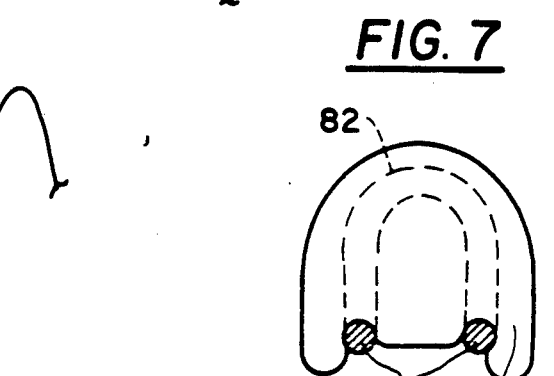
FIG. 7 is a top plan view of the insert of FIG. 6.
Figure 8:
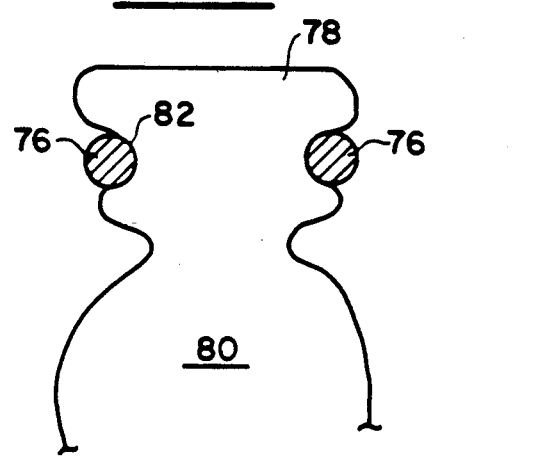
FIG. 8 is a proximal view of the insert of FIG. 6.

Each proximal insert 14 has a main body portion 20 adapted to fill a portion of the proximal box 22 of the cavity 10 and to provide a contact area 24 for the next adjacent tooth 18, and a connector portion 26. A reduced thickness or necked down, isthmus portion 28 interconnects the main body portion 20 and the connector portion 26 and allows the latter two portions to be severed during the later stags of the filling process. A relatively rigid spring element 30 is coupled to the connector portion 26 and extends from the connector portion 26, terminating distally in a terminal portion 32 an a distorted end 34. The terminal portion 32 is adapted to be coupled to a sure contact appliance in accordance with the invention. In the alternative, spring 30 can be configured so that its distal end can be abutted against the healthy portion of tooth 16, as at 84 in FIG. 5. As is apparent, distortion of spring 30 will vary the gap between insert body 14 and the insert element or end 84 to thereby ensure that insert 14 is positively urged towards adjacent tooth 18. In the illustrated embodiment, the spring element 30 is partially embedded in the connector portion. However, the spring element can be detachably coupled to the connector portion. For example, the spring element (s) 76 can engage the connector portion 78 of the insert 80 in a U-shaped preformed horizontal recess 82 and be inserted bilaterally into the mounting element (FIGS. 6–8).

The spring element 30 may be metal or plastic and is provided to resiliently urge the insert 14 into contact, directly or indirectly, with adjacent tooth material 18. In the preferred embodiment the spring element 30 is formed from metal so that it is at least slightly malleable. Accordingly, if desired, the orientation, position and urging force of the insert 14 can be finely adjusted. Thus, by way of example, the spring element 30 can be, at lea in part, a round or rectangular wire or in the form of an elongated flat plate spring.

Each occlusal insert 12 similarly has a main body portion 36 adapted to fill a portion of the cavity 10 and to abut, directly or indirectly, the healthy portion of the tooth 16, and a connector portion 38. A reduced thickness or necked down, isthmus portion 40 interconnects the main body portion 36 and the connector portion 38 of the occlusal insert 12 and allows the latter two portions to be severed during the filling process. A relatively rigid spring element 42 is partially embedded in and extends from the connector portion 38 and terminates in a terminal portion 44 and is a distorted end 46. The terminal portion 44 is adapted to be coupled to a sure contact appliance in accordance with the invention. Again, the spring element 42 may be metal or plastic and is provided to resiliently urge the insert 12 into the desired contact with adjacent tooth material. In the preferred embodiment, the spring element is formed from metal, such as a wire or a flat plate spring, so that the orientation, position and urging force of the insert 12 can be finely adjusted.

One embodiment of a sure contact appliance 48 in accordance with the invention is shown in FIG. 2. That appliance includes two mounting elements 50,52, each of which is adapted to be interconnected with the spring element of an insert of the invention. The spring element of each inset and, in particular, the terminal portion of the spring element can be coupled to the respective mounting element 50,52 in any suitable manner, unilaterally or bilaterally, including permanent interconnection if so desired. Preferably simple frictional engagement is relied upon. For example, a bore (not shown in particular) can be defined in each mounting element for slidably receiving and frictionally retaining a respective spring element. In the alternative, a coupling element can be defined on the mounting element. The coupling element can be tubular as shown at 54, having a cross-sectional shape accommodating that of the spring element so that coupling can be effected by sliding the spring terminal portion through the connector tube and then distorting the distalmost end of the spring (to form distorted end 35,46) so that sliding removal is prevented, while frictional engagement and corresponding rectangular shape prevents relative rotation.

As yet a further alternative, the coupling element can be mounted to the under surface of the mounting elements (only on of which is shown in FIG. 3) so that the sure contact appliance sits on top of the spring elements 30,42 and insert(s) 14,12 whereby torque on the inserts which would tend to rotate them out of position is avoided.

A U-shaped coupling element 56 may be alternatively mounted to the side face of the mounting element(s) as is also shown in FIG. 3. Where the coupling element 56 is side mounted, a gate member 58 can be provided to maintain the spring element therewithin in the event the mounting element is inadvertently bumped or rotates sideways under its own weight. If desired, furthermore, a guard 60 can capture the edge of the gate. Otherwise, forming the connector element 56 as a spring clip will retain the spring terminal portion in a desired position. In any event, the distorted end of the spring element and providing a terminal portion on the spring element which has a length corresponding to the length of the coupling element will insure that undesired detachment and relative movement is avoided and a stable assembly is provided.

A stabilizer bar 62 is mounted to one of the mounting elements and extends through a suitably defined aperture 64 in the other of the mounting elements. The stabilizer bar 62 maintains the mounting elements in a desired orientation with respect to one another and, in particular, insures that the insets will be maintained in a desired orientation and a uniform and predictable motion of the inserts relative to one another will be obtained.

Adjustment of the spacing of the inserts and of the pressure applied by the proximal inset 14 against the adjacent tooth 18 is effected with a threaded shaft 66 which is mounted through a threaded bore 68 defined in one of the mounting elements and which abuts the other of the mounting elements. When the threaded shaft 66 is rotated clockwise, in the direction of arrow A, the shaft 66 is advanced through the threaded bore 68 of mounting element 52 and thus advances toward mounting element 50. Because the shaft 66 abuts mounting element 50, that mounting element is urged away from mounting element 52 so that the occlusal inset 12 and the proximal insert 14 are moved apart by an amount equal to or the urging force of the insets against the preexisting tooth material increases by an amount that is a function of the axial movement of the shaft 66 as a result of said rotation.

Once the shaft has been rotated a desired amount, then, the proximal and occlusal inserts 14,12 will be spaced apart a desired amount and will be positively urged via the spring elements 30,42 against the adjacent tooth 18 and the healthy material of the tooth 16 being filled, respectively. The appliance is now set to maintain the inserts in that desired position and apply that desired constant positive pressure against adjacent surfaces. It is to be removed from the mouth to allow the placement of the unpolymerized resin in the areas where the inserts will be. The appliance is then placed back into the present position thus enabling the inserts to displace and condense the unpolymerized resin around them. Overflowing resin is removed away from the margins and polymerization is begun.

Once the filling process has been substantially completed, the sure contact appliance is detached from the inserts by severing at the isthmus portions of the inserts so that embedded portion of the insert will remain in the thus filled cavity.

The filling process utilizing the device of FIGS. 1 and 2 is as follows. Once the cavity 10 is prepared, suitable inserts 14 and 12 are selected and are trimmed as required to allow for a loose fit where the level of the contact area(s) and marginal ridge(s) conform to the marginal anatomy of the tooth. The inserts are then treated with silaine.

An ultra thin matrix 70 that can be easily burnished is then inserted. The band is burnished and trimmed at the height of the marginal ridge. A wedge 72 is used to avoid marginal overhang and minimize the danger of moisture contamination around the gingival margin. The inserts (one proximal and one occlusal or two proximal for MOD cavities) are then mounted on a sure contact appliance 48 provided in accordance with the invention and placed in the empty cavity 10. A desired contact pressure is obtained by turning the position adjusting screw clockwise. (Arrow A) The contact point 24 is then checked with dental floss, the wedge 72 is adjusted and then the appliance 48 and insert 12,14 combination are pulled occlusally out of the mouth. The cavity 10 is then checked for dryness and proper etching of the enamel.

An unpolymerized chemical, light or dual cured, composite is then pressed in the proximal box 22 and where the occlusal insert 12 will go. The appliance/insert combination is then gently pushed back in place and the extruded composite is packed well between the cavity walls and the inserts. The composite/insert complex is then cured.

The dentist then proceeds with filling the remainder of the cavity. Once the cavity filling process has been or is substantially completed, the matrix 70 and wedge 72 are generally removed. The polymerizing light is then reactivated to maximized polymerization in the area(s) which were previously covered by the matrix band. The necked down or isthmus portions 28,40 are then severed. Such cutting can be accomplished with a thin diamond mounted on a high speed handpiece. The occlusal surface is then carved, finished and polished.

The contact providing insert of the invention overcomes many of the disadvantages of the direct technique and enhances the advantages thereof simultaneously.

Indeed, the insert provided in accordance with the present invention minimizes the effects of polymerization shrinkage, improves the durability and wear resistance of the composite restoration.

It ensures that the proximal contact area is predetermined, prepositioned and maintained during the filling process. Interproximal contact is guaranteed to be tight because of the positive constant pressure exerted by insert against the adjacent proximal surface. The greater durability of the insert of the invention guarantees that contact will not wear faster than normal. In addition, the restored marginal ridge will be more resistant to wear. Therefore, development of a plunger cusp in this area is significantly less likely.

Until we get an ideal filling material this invention combined with these filling materials should make is easier, faster and less expensive to acquire a durable long lasting, esthetic restoration for cavities involving proximal decay. It is totally logical to expect that this technique will offset the need for the destruction of sound tooth structure which often occurs in the process of reducing teeth for extensive restorations such as crowns and onlays. Instead, we may now think in terms of precision contact inserts.

While the invention has been described in connection with what is presently considered to be the most practical and preferred embodiments, it is to be understood that the invention is not limited to the disclosed embodiment, but, on the contrary, is intended to cover various modifications and equivalent arrangements included within the spirit and scope of the appended claims.

What is claimed is:

1. An assembly for use in restoring a tooth and for forming a contact area with a next adjacent tooth comprising:
   a pre-formed, relatively rigid insert body having a side face adapted to face outwardly from a cavity being filled towards a tooth adjacent to the tooth being restored, said outwardly facing side face defining a convex portion for providing a contact area with the adjacent tooth; and
   means for urging the insert body towards the next adjacent tooth with a constant, predetermined force whereby the restored tooth and the next adjacent tooth will have a natural disposition with said insert body firmly and predeterminately positioned in the cavity of the restored tooth and immediately adjacent said adjacent tooth and substantially in contact therewith, said means for urging comprising spring means.

2. An assembly as in claim 1, wherein said spring means operatively engages the tooth being restored and urges said insert body with respect thereto.

3. An assembly as in claim 1, wherein an urging force of said spring means is selectively variable.

4. An assembly as in claim 1, wherein said spring means includes a flat plate spring element.

5. An assembly as in claim 1, wherein said insert body includes a main body portion adapted to be embedded in the filled cavity, a connector portion to which said means for urging is operatively coupled and a reduced diameter, isthmus portion, whereby said means for urging can be severed from said insert body by severing said insert body at said isthmus portion.

6. An assembly as in claim 1, further comprising an insert element, the insert body and the insert element being mounted in spaced relation to one another, said means for urging including an appliance comprising first and second mounting elements and first and second spring elements, one of said spring elements being operatively coupled to said insert body and to said first mounting element, and the other of said spring elements being operatively coupled to said insert element and to said second mounting element, one of said mounting elements having a threaded bore therethrough and a threaded shaft threadably engaged in said bore, said threaded shaft abutting the other of said mounting elements whereby rotation of said shaft moves said mounting elements relative to one another to thereby vary one of a gap between said insert body and said insert element and a force exerted by said insert body against the adjacent tooth.

7. An assembly for use in restoring a tooth and for forming a contact area with a next adjacent tooth comprising:
   a pre-formed, relatively rigid insert body having a side face adapted to face outwardly from a cavity being filled towards a tooth adjacent to the tooth being restored, said outwardly facing side face defining a convex portion for providing a contact area with the adjacent tooth; and
   means for urging the insert body towards the next adjacent tooth with a constant, predetermined force whereby the restored tooth and the next adjacent tooth will have a natural disposition with said insert body firmly and predeterminately positioned in the cavity of the restored tooth and immediately adjacent said adjacent tooth and substantially in contact therewith; and
   an insert element, the inset body and the insert element being mounted in spaced relation to one another, a gap between said insert body and said insert element being adjustable.

8. An assembly as in claim 7, wherein said insert body includes a main body portion adapted to be embedded in the filled cavity, a connector portion to which said means for urging is operatively coupled and a reduced diameter, isthmus portion, whereby said means for urging can be severed from said insert body by severing said insert body at said isthmus portion.

9. An assembly as in claim 7, wherein adjustment of said gap varies an urging force of said insert body against the next adjacent tooth.

10. An assembly as in claim 7, wherein said means for urging comprises spring means.

11. An assembly as in claim 10, wherein said spring means includes a flat plate spring element.

12. A method of restoring a tooth comprising:
    preparing a cavity in the tooth to be restored for filling;
    selecting an insert body for providing a contact area with an adjacent tooth and a means for urging the insert body towards the next adjacent tooth with a constant, predetermined force, said means for urging comprising spring means;
    depositing an unpolymerized chemical, light or dual cured, composite at least in the portion of the cavity where the insert body is to be inserted;
    pushing the insert body into place and packing the composite between the cavity walls and the insert;
    curing the composite/insert body complex; and
    filling the remainder of the cavity.

13. A method as in claim 12, further comprising detaching said insert body from said urging means.

14. A method as in claim 12, further comprising the use of a dental matrix band & wedge in combination with the urged insert body to mold the proximal anatomy of the restoration.

15. A method of restoring a tooth comprising:
    preparing a cavity in the tooth to be restored for filling;
    selecting an insert body for providing a contact area with an adjacent tooth and an insert element, the insert body and the insert element being mounted in spaced relation to one another, and means for adjusting a gap between said insert body and said insert element so as to urge the insert body towards the next adjacent tooth with a constant predetermined face;
    depositing an unpolymerized chemical, light or dual cured, composite at least in the portion of the cavity where the insert body is to be inserted;
    pushing the insert body into place and packing the composite between the cavity walls and the insert;
    curing the composite/insert body complex; and
    filling the remainder of the cavity.

16. A method as in claim 15, further comprising detaching said insert body from said insert element and said means for adjusting.

17. A method as in claim 15, further comprising the use of a dental matrix band and wedge in combination with the urged insert body to mold the proximal anatomy of the restoration.

* * * * *